US007892592B1

(12) United States Patent
Chen et al.

(10) Patent No.: US 7,892,592 B1
(45) Date of Patent: Feb. 22, 2011

(54) COATING ABLUMINAL SURFACES OF STENTS AND OTHER IMPLANTABLE MEDICAL DEVICES

(75) Inventors: Yung Ming Chen, Cupertino, CA (US); Jeff H. Smith, Newark, CA (US); Celenia Gutierrez, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1544 days.

(21) Appl. No.: 11/000,799

(22) Filed: Nov. 30, 2004

(51) Int. Cl.
*B05D 3/00* (2006.01)
*A61L 33/00* (2006.01)
*B05C 13/00* (2006.01)

(52) U.S. Cl. ...................... 427/2.1; 427/2.24; 427/2.25; 118/500; 118/504; 118/505

(58) Field of Classification Search .................. 427/2.1, 427/2.24, 256; 118/500, 503, 320
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 3,996,938 A | 12/1976 | Clark, III | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,629,563 A | 12/1986 | Wrasidlo | |
| 4,656,242 A | 4/1987 | Swan et al. | |
| 4,733,665 A | 3/1988 | Palmaz | |
| 4,762,128 A * | 8/1988 | Rosenbluth | 606/192 |
| 4,800,882 A | 1/1989 | Gianturco | |
| 4,882,168 A | 11/1989 | Casey et al. | |

(Continued)

FOREIGN PATENT DOCUMENTS

DE 42 24 401 1/1994

(Continued)

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Timothy H Meeks
*Assistant Examiner*—Cachet I Sellman
(74) *Attorney, Agent, or Firm*—Squire, Sanders & Dempsey (US) LLP

(57) ABSTRACT

A sleeve is positioned over a radially-expandable rod assembly and a stent is positioned over the sleeve. A mandrel is inserted into the rod assembly to thereby press the sleeve against the inner surface of the stent and expand the stent. A coating (such as a solvent, a polymer and/or a therapeutic substance) is then applied to the outer (abluminal) surfaces of the stent, by spraying, for example. The sleeve advantageously prevents the coating material from being applied to inner (luminal) surfaces of the stent and also allows the coating material to be efficiently applied to the abluminal surfaces.

30 Claims, 4 Drawing Sheets

U.S. PATENT DOCUMENTS

| | | | |
|---|---|---|---|
| 4,886,062 | A | 12/1989 | Wiktor |
| 4,893,623 | A | 1/1990 | Rosenbluth |
| 4,906,423 | A | 3/1990 | Frisch |
| 4,931,287 | A | 6/1990 | Bae et al. |
| 4,941,870 | A | 7/1990 | Okada et al. |
| 4,955,899 | A | 9/1990 | Della Corna et al. |
| 4,977,901 | A | 12/1990 | Ofstead |
| 5,019,096 | A | 5/1991 | Fox, Jr. et al. |
| 5,037,427 | A | 8/1991 | Harada et al. |
| 5,061,275 | A | 10/1991 | Wallsten et al. |
| 5,100,992 | A | 3/1992 | Cohn et al. |
| 5,112,457 | A | 5/1992 | Marchant |
| 5,133,742 | A | 7/1992 | Pinchuk |
| 5,163,952 | A | 11/1992 | Froix |
| 5,165,919 | A | 11/1992 | Sasaki et al. |
| 5,171,445 | A | 12/1992 | Zepf |
| 5,188,734 | A | 2/1993 | Zepf |
| 5,217,482 | A | 6/1993 | Keith |
| 5,219,980 | A | 6/1993 | Swidler |
| 5,229,045 | A | 7/1993 | Soldani |
| 5,234,457 | A | 8/1993 | Andersen |
| 5,258,020 | A | 11/1993 | Froix |
| 5,272,012 | A | 12/1993 | Opolski |
| 5,292,516 | A | 3/1994 | Viegas et al. |
| 5,298,260 | A | 3/1994 | Viegas et al. |
| 5,300,295 | A | 4/1994 | Viegas et al. |
| 5,306,501 | A | 4/1994 | Viegas et al. |
| 5,306,786 | A | 4/1994 | Moens et al. |
| 5,328,471 | A | 7/1994 | Slepian |
| 5,330,768 | A | 7/1994 | Park et al. |
| 5,363,881 | A | 11/1994 | Larkin |
| 5,380,299 | A | 1/1995 | Fearnot et al. |
| 5,417,981 | A | 5/1995 | Endo et al. |
| 5,447,724 | A | 9/1995 | Helmus et al. |
| 5,455,040 | A | 10/1995 | Marchant |
| 5,462,990 | A | 10/1995 | Hubbell et al. |
| 5,464,650 | A | 11/1995 | Berg et al. |
| 5,485,496 | A | 1/1996 | Lee et al. |
| 5,516,881 | A | 5/1996 | Lee et al. |
| 5,537,729 | A | 7/1996 | Kolobow |
| 5,569,463 | A | 10/1996 | Helmus et al. |
| 5,578,073 | A | 11/1996 | Haimovich et al. |
| 5,584,877 | A | 12/1996 | Miyake et al. |
| 5,605,696 | A | 2/1997 | Eury et al. |
| 5,607,467 | A | 3/1997 | Froix |
| 5,609,629 | A | 3/1997 | Fearnot et al. |
| 5,610,241 | A | 3/1997 | Lee et al. |
| 5,611,775 | A | 3/1997 | Machold et al. |
| 5,616,338 | A | 4/1997 | Fox, Jr. et al. |
| 5,624,411 | A | 4/1997 | Tuch |
| 5,628,730 | A | 5/1997 | Shapland et al. |
| 5,628,786 | A | 5/1997 | Banas et al. |
| 5,644,020 | A | 7/1997 | Timmermann et al. |
| 5,649,977 | A | 7/1997 | Campbell |
| 5,658,995 | A | 8/1997 | Kohn et al. |
| 5,667,767 | A | 9/1997 | Greff et al. |
| 5,670,558 | A | 9/1997 | Onishi et al. |
| 5,674,242 | A | 10/1997 | Phan et al. |
| 5,679,400 | A | 10/1997 | Tuch |
| 5,700,286 | A | 12/1997 | Tartaglia et al. |
| 5,702,754 | A | 12/1997 | Zhong |
| 5,711,958 | A | 1/1998 | Cohn et al. |
| 5,716,981 | A | 2/1998 | Hunter et al. |
| 5,721,131 | A | 2/1998 | Rudolph et al. |
| 5,723,219 | A | 3/1998 | Kolluri et al. |
| 5,735,897 | A | 4/1998 | Buirge |
| 5,746,998 | A | 5/1998 | Torchilin et al. |
| 5,759,205 | A | 6/1998 | Valentini |
| 5,772,864 | A | 6/1998 | Møller et al. |
| 5,776,184 | A | 7/1998 | Tuch |
| 5,783,657 | A | 7/1998 | Pavlin et al. |
| 5,788,626 | A | 8/1998 | Thompson |
| 5,788,979 | A | 8/1998 | Alt et al. |
| 5,800,392 | A | 9/1998 | Racchini |
| 5,820,917 | A | 10/1998 | Tuch |
| 5,823,996 | A | 10/1998 | Sparks |
| 5,824,048 | A | 10/1998 | Tuch |
| 5,824,049 | A | 10/1998 | Ragheb et al. |
| 5,830,178 | A | 11/1998 | Jones et al. |
| 5,833,659 | A | 11/1998 | Kranys |
| 5,837,008 | A | 11/1998 | Berg et al. |
| 5,837,313 | A | 11/1998 | Ding et al. |
| 5,849,859 | A | 12/1998 | Acemoglu |
| 5,851,508 | A | 12/1998 | Greff et al. |
| 5,854,376 | A | 12/1998 | Higashi |
| 5,855,598 | A | 1/1999 | Pinchuk |
| 5,858,746 | A | 1/1999 | Hubbell et al. |
| 5,865,814 | A | 2/1999 | Tuch |
| 5,869,127 | A | 2/1999 | Zhong |
| 5,873,904 | A | 2/1999 | Ragheb et al. |
| 5,876,433 | A | 3/1999 | Lunn |
| 5,877,224 | A | 3/1999 | Brocchini et al. |
| 5,879,499 | A | 3/1999 | Corvi |
| 5,879,713 | A | 3/1999 | Roth et al. |
| 5,895,407 | A | 4/1999 | Jayaraman |
| 5,897,911 | A | 4/1999 | Loeffler |
| 5,902,875 | A | 5/1999 | Roby et al. |
| 5,905,168 | A | 5/1999 | Dos Santos et al. |
| 5,910,564 | A | 6/1999 | Gruning et al. |
| 5,914,387 | A | 6/1999 | Roby et al. |
| 5,919,893 | A | 7/1999 | Roby et al. |
| 5,922,393 | A | 7/1999 | Jayaraman |
| 5,925,720 | A | 7/1999 | Kataoka et al. |
| 5,932,299 | A | 8/1999 | Katoot |
| 5,935,135 | A | 8/1999 | Bramfitt et al. |
| 5,948,018 | A | 9/1999 | Dereume et al. |
| 5,955,509 | A | 9/1999 | Webber et al. |
| 5,958,385 | A | 9/1999 | Tondeur et al. |
| 5,962,138 | A | 10/1999 | Kolluri et al. |
| 5,971,954 | A | 10/1999 | Conway et al. |
| 5,980,928 | A | 11/1999 | Terry |
| 5,980,972 | A | 11/1999 | Ding |
| 5,997,517 | A | 12/1999 | Whitbourne |
| 6,010,530 | A | 1/2000 | Goicoechea |
| 6,010,573 | A | 1/2000 | Bowlin |
| 6,011,125 | A | 1/2000 | Lohmeijer et al. |
| 6,015,541 | A | 1/2000 | Greff et al. |
| 6,033,582 | A | 3/2000 | Lee et al. |
| 6,034,204 | A | 3/2000 | Mohr et al. |
| 6,042,875 | A | 3/2000 | Ding et al. |
| 6,045,899 | A | 4/2000 | Wang et al. |
| 6,051,576 | A | 4/2000 | Ashton et al. |
| 6,051,648 | A | 4/2000 | Rhee et al. |
| 6,054,553 | A | 4/2000 | Groth et al. |
| 6,056,993 | A | 5/2000 | Leidner et al. |
| 6,060,451 | A | 5/2000 | DiMaio et al. |
| 6,060,518 | A | 5/2000 | Kabanov et al. |
| 6,080,488 | A | 6/2000 | Hostettler et al. |
| 6,096,070 | A | 8/2000 | Ragheb et al. |
| 6,099,562 | A | 8/2000 | Ding et al. |
| 6,110,188 | A | 8/2000 | Narciso, Jr. |
| 6,110,483 | A | 8/2000 | Whitbourne et al. |
| 6,113,629 | A | 9/2000 | Ken |
| 6,120,491 | A | 9/2000 | Kohn et al. |
| 6,120,536 | A | 9/2000 | Ding et al. |
| 6,120,788 | A | 9/2000 | Barrows |
| 6,120,847 | A | 9/2000 | Yang et al. |
| 6,120,904 | A | 9/2000 | Hostettler et al. |
| 6,121,027 | A | 9/2000 | Clapper et al. |
| 6,126,686 | A | 10/2000 | Badylak et al. |
| 6,129,761 | A | 10/2000 | Hubbell |
| 6,136,333 | A | 10/2000 | Cohn et al. |
| 6,143,354 | A | 11/2000 | Koulik et al. |
| 6,153,252 | A | 11/2000 | Hossainy et al. |

| | | | |
|---|---|---|---|
| 6,156,373 | A | 12/2000 | Zhong et al. |
| 6,159,978 | A | 12/2000 | Myers et al. |
| 6,165,212 | A | 12/2000 | Dereume et al. |
| 6,172,167 | B1 | 1/2001 | Stapert et al. |
| 6,177,523 | B1 | 1/2001 | Reich et al. |
| 6,180,632 | B1 | 1/2001 | Myers et al. |
| 6,203,551 | B1 | 3/2001 | Wu |
| 6,211,249 | B1 | 4/2001 | Cohn et al. |
| 6,214,115 | B1 | 4/2001 | Taylor et al. |
| 6,214,901 | B1 | 4/2001 | Chudzik et al. |
| 6,231,600 | B1 | 5/2001 | Zhong |
| 6,240,616 | B1 | 6/2001 | Yan |
| 6,245,099 | B1 | 6/2001 | Edwin et al. |
| 6,245,753 | B1 | 6/2001 | Byun et al. |
| 6,245,760 | B1 | 6/2001 | He et al. |
| 6,248,129 | B1 | 6/2001 | Froix |
| 6,251,136 | B1 | 6/2001 | Guruwaiya et al. |
| 6,254,632 | B1 | 7/2001 | Wu et al. |
| 6,258,121 | B1 | 7/2001 | Yang et al. |
| 6,258,371 | B1 | 7/2001 | Koulik et al. |
| 6,262,034 | B1 | 7/2001 | Mathiowitz et al. |
| 6,270,788 | B1 | 8/2001 | Koulik et al. |
| 6,277,449 | B1 | 8/2001 | Kolluri et al. |
| 6,279,368 | B1 | 8/2001 | Escano et al. |
| 6,283,947 | B1 | 9/2001 | Mirzaee |
| 6,283,949 | B1 | 9/2001 | Roorda |
| 6,284,305 | B1 | 9/2001 | Ding et al. |
| 6,287,628 | B1 | 9/2001 | Hossainy et al. |
| 6,299,604 | B1 | 10/2001 | Ragheb et al. |
| 6,306,176 | B1 | 10/2001 | Whitbourne |
| 6,322,847 | B1 | 11/2001 | Zhong et al. |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,364,903 | B2 | 4/2002 | Tseng et al. |
| 6,379,381 | B1 | 4/2002 | Hossainy et al. |
| 6,387,118 | B1 | 5/2002 | Hanson |
| 6,387,379 | B1 | 5/2002 | Goldberg et al. |
| 6,395,326 | B1 | 5/2002 | Castro et al. |
| 6,419,692 | B1 | 7/2002 | Yang et al. |
| 6,451,373 | B1 | 9/2002 | Hossainy et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |
| 6,521,284 | B1 | 2/2003 | Parsons et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,540,776 | B2 | 4/2003 | Sanders Millare et al. |
| 6,544,223 | B1 | 4/2003 | Kokish |
| 6,544,543 | B1 | 4/2003 | Mandrusov et al. |
| 6,544,582 | B1 | 4/2003 | Yoe |
| 6,555,157 | B1 | 4/2003 | Hossainy |
| 6,558,733 | B1 | 5/2003 | Hossainy et al. |
| 6,565,659 | B1 | 5/2003 | Pacetti et al. |
| 6,572,644 | B1 | 6/2003 | Moein |
| 6,585,755 | B2 | 7/2003 | Jackson et al. |
| 6,585,765 | B1 | 7/2003 | Hossainy et al. |
| 6,585,926 | B1 | 7/2003 | Mirzaee |
| 6,605,110 | B2 | 8/2003 | Harrison |
| 6,605,154 | B1 | 8/2003 | Villareal |
| 6,610,087 | B1 | 8/2003 | Zarbatany et al. |
| 6,616,765 | B1 | 9/2003 | Hossaony et al. |
| 6,623,448 | B2 | 9/2003 | Slater |
| 6,625,486 | B2 | 9/2003 | Lundkvist et al. |

| | | | |
|---|---|---|---|
| 6,645,135 | B1 | 11/2003 | Bhat |
| 6,645,195 | B1 | 11/2003 | Bhat et al. |
| 6,656,216 | B1 | 12/2003 | Hossainy et al. |
| 6,656,506 | B1 | 12/2003 | Wu et al. |
| 6,660,034 | B1 | 12/2003 | Mandrusov et al. |
| 6,663,662 | B2 | 12/2003 | Pacetti et al. |
| 6,663,880 | B1 | 12/2003 | Roorda et al. |
| 6,666,880 | B1 | 12/2003 | Chiu et al. |
| 6,669,980 | B2 | 12/2003 | Hansen |
| 6,673,154 | B1 | 1/2004 | Pacetti et al. |
| 6,673,385 | B1 | 1/2004 | Ding et al. |
| 6,676,700 | B1 | 1/2004 | Jacobs et al. |
| 6,689,099 | B2 | 2/2004 | Mirzaee |
| 6,695,920 | B1 | 2/2004 | Pacetti et al. |
| 6,706,013 | B1 | 3/2004 | Bhat et al. |
| 6,709,514 | B1 | 3/2004 | Hossainy |
| 6,712,845 | B2 | 3/2004 | Hossainy |
| 6,713,119 | B2 | 3/2004 | Hossainy et al. |
| 6,716,444 | B1 | 4/2004 | Castro et al. |
| 6,723,120 | B2 | 4/2004 | Yan |
| 6,733,768 | B2 | 5/2004 | Hossainy et al. |
| 6,740,040 | B1 | 5/2004 | Mandrusov et al. |
| 6,743,462 | B1 | 6/2004 | Pacetti |
| 6,746,773 | B2 | 6/2004 | Llanos et al. |
| 6,749,626 | B1 | 6/2004 | Bhat et al. |
| 6,753,071 | B1 | 6/2004 | Pacetti |
| 6,758,859 | B1 | 7/2004 | Dang et al. |
| 6,759,054 | B2 | 7/2004 | Chen et al. |
| 6,764,505 | B1 | 7/2004 | Hossainy et al. |
| 6,883,546 | B1 | 4/2005 | Kobylinski |
| 7,011,675 | B2 | 3/2006 | Hemerick et al. |
| 7,048,962 | B2 | 5/2006 | Shekalim et al. |
| 7,198,675 | B2 * | 4/2007 | Fox et al. .................... 118/500 |
| 7,211,150 | B1 | 5/2007 | Kokish et |
| 7,338,557 | B1 | 3/2008 | Chen et al. |
| 2001/0007083 | A1 | 7/2001 | Roorda |
| 2001/0014717 | A1 | 8/2001 | Hossainy et al. |
| 2001/0018469 | A1 | 8/2001 | Chen et al. |
| 2001/0020011 | A1 | 9/2001 | Mathiowitz et al. |
| 2001/0029351 | A1 | 10/2001 | Falotico et al. |
| 2001/0037145 | A1 | 11/2001 | Guruwaiya et al. |
| 2001/0051608 | A1 | 12/2001 | Mathiowitz et al. |
| 2002/0005206 | A1 | 1/2002 | Falotico et al. |
| 2002/0007213 | A1 | 1/2002 | Falotico et al. |
| 2002/0007214 | A1 | 1/2002 | Falotico |
| 2002/0007215 | A1 | 1/2002 | Falotico et al. |
| 2002/0009604 | A1 | 1/2002 | Zamora et al. |
| 2002/0016625 | A1 | 2/2002 | Falotico et al. |
| 2002/0032414 | A1 | 3/2002 | Ragheb et al. |
| 2002/0032434 | A1 | 3/2002 | Chudzik et al. |
| 2002/0051730 | A1 | 5/2002 | Bodnar et al. |
| 2002/0071822 | A1 | 6/2002 | Uhrich |
| 2002/0077693 | A1 | 6/2002 | Barclay et al. |
| 2002/0082679 | A1 | 6/2002 | Sirhan et al. |
| 2002/0087123 | A1 | 7/2002 | Hossainy et al. |
| 2002/0091433 | A1 | 7/2002 | Ding et al. |
| 2002/0094440 | A1 | 7/2002 | Llanos et al. |
| 2002/0111590 | A1 | 8/2002 | Davila et al. |
| 2002/0120326 | A1 | 8/2002 | Michal |
| 2002/0123801 | A1 | 9/2002 | Pacetti et al. |
| 2002/0142039 | A1 | 10/2002 | Claude |
| 2002/0155212 | A1 | 10/2002 | Hossainy |
| 2002/0165608 | A1 | 11/2002 | Llanos et al. |
| 2002/0176849 | A1 | 11/2002 | Slepian |
| 2002/0183581 | A1 | 12/2002 | Yoe et al. |
| 2002/0188037 | A1 | 12/2002 | Chudzik et al. |
| 2002/0188277 | A1 | 12/2002 | Roorda et al. |
| 2003/0004141 | A1 | 1/2003 | Brown |
| 2003/0028243 | A1 | 2/2003 | Bates et al. |
| 2003/0028244 | A1 | 2/2003 | Bates et al. |
| 2003/0031780 | A1 | 2/2003 | Chudzik et al. |
| 2003/0032767 | A1 | 2/2003 | Tada et al. |
| 2003/0036794 | A1 | 2/2003 | Ragheb et al. |

| | | | |
|---|---|---|---|
| 2003/0039689 A1 | 2/2003 | Chen et al. | |
| 2003/0040712 A1 | 2/2003 | Ray et al. | |
| 2003/0040790 A1 | 2/2003 | Furst | |
| 2003/0059520 A1 | 3/2003 | Chen et al. | |
| 2003/0060877 A1 | 3/2003 | Falotico et al. | |
| 2003/0065377 A1 | 4/2003 | Davila et al. | |
| 2003/0072868 A1 | 4/2003 | Harish et al. | |
| 2003/0073961 A1 | 4/2003 | Happ | |
| 2003/0083646 A1* | 5/2003 | Sirhan et al. | 604/891.1 |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099712 A1 | 5/2003 | Jayaraman | |
| 2003/0105518 A1 | 6/2003 | Dutta | |
| 2003/0113439 A1 | 6/2003 | Pacetti et al. | |
| 2003/0139800 A1 | 7/2003 | Campbell | |
| 2003/0143315 A1 | 7/2003 | Pui et al. | |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2003/0215564 A1 | 11/2003 | Heller et al. | |
| 2004/0013792 A1 | 1/2004 | Epstein | |
| 2004/0018296 A1 | 1/2004 | Castro et al. | |
| 2004/0029952 A1 | 2/2004 | Chen et al. | |
| 2004/0047978 A1 | 3/2004 | Hossainy et al. | |
| 2004/0047980 A1 | 3/2004 | Pacetti et al. | |
| 2004/0052858 A1 | 3/2004 | Wu et al. | |
| 2004/0052859 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072922 A1 | 4/2004 | Hossainy et al. | |
| 2004/0073298 A1 | 4/2004 | Hossainy | |
| 2004/0086542 A1 | 5/2004 | Hossainy et al. | |
| 2004/0086550 A1 | 5/2004 | Roorda et al. | |
| 2004/0096504 A1 | 5/2004 | Michal | |
| 2004/0098117 A1 | 5/2004 | Hossainy et al. | |
| 2004/0098118 A1 | 5/2004 | Granada et al. | |
| 2004/0142015 A1 | 7/2004 | Hossainy | |
| 2004/0197501 A1* | 10/2004 | Sridharan | 428/35.2 |
| 2005/0113799 A1* | 5/2005 | Lenker | 604/509 |
| 2006/0029720 A1* | 2/2006 | Panos et al. | 427/2.1 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | WO 98/17331 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 07-60385 | 3/1995 |
| JP | 2001-190687 | 7/2001 |
| SU | 872531 | 10/1981 |
| SU | 876663 | 10/1981 |
| SU | 905228 | 10/1982 |
| SU | 790725 | 2/1983 |
| SU | 1016314 | 5/1983 |
| SU | 811750 | 9/1983 |
| SU | 1293518 | 2/1987 |
| SU | EP 0 301 856 | 2/1988 |
| SU | EP 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/32398 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/051490 | 7/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/037223 | 3/2003 |
| WO | WO 03/028780 | 4/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

PUBLICATIONS

Anonymous, *Heparin-coated stents cut complications by 30%*, Clinica 732:17 Nov. 18, 1996), http://www.dialogweb.com/cci/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

COATING ABLUMINAL SURFACES OF STENTS AND OTHER IMPLANTABLE MEDICAL DEVICES

BACKGROUND OF THE INVENTION

Blood vessel occlusions are commonly treated by mechanically enhancing blood flow in the affected vessels, such as by employing a stent. Stents act as scaffoldings, physically holding open and, if desired, expanding the wall of affected vessels. Typically, stents are capable of being compressed, so that they can be inserted through small lumens via catheters, and then expanded to a larger diameter once they are at the desired location. Examples of patents disclosing stents include U.S. Pat. Nos. 4,733,665 (Palmaz), 4,800,882 (Gianturco), 4,886,062 (Wiktor), 5,061,275 (Wallstein) and 6,605,110 (Harrison), and US 2003/0139800 1 (Campbell). (The entire contents of all patents and other publications and U.S. patent applications mentioned anywhere in this disclosure are hereby incorporated by reference.)

FIG. 1 illustrates a conventional stent shown generally at 100 formed from a plurality of structural elements including struts 120 and connecting elements. The struts 120 can be radially expandable and interconnected by connecting elements that are disposed between adjacent struts 120, leaving lateral openings or gaps 160 between the adjacent struts. Struts 120 and connecting elements define a tubular stent body having an outer, tissue-contacting surface (an abluminal surface) and an inner surface (a luminal surface).

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered compared to systemic dosages that often produce adverse or even toxic side effects for the patient.

One method of medicating a stent uses a polymeric carrier coated onto the surface of the stent. A composition including a solvent, a polymer dissolved in the solvent, and a therapeutic substance dispersed in the blend can be applied to the stent by immersing the stent in the composition or by spraying the composition onto the stent. The solvent is allowed to evaporate, leaving on the surfaces a coating of the polymer and the therapeutic substance impregnated in the polymer.

The dipping or spraying of the composition onto the stent can result in a complete coverage of all stent surfaces, that is, both luminal (inner) and abluminal (outer) surfaces, with a coating. However, from a therapeutic standpoint, drugs need only be released from the abluminal stent surface, and possibly the sidewalls. Moreover, having a coating on the luminal surfaces of the stent can detrimentally impact the stent's deliverability as well as the coating's mechanical integrity. A polymeric coating can increase the coefficient of friction between the stent and the delivery balloon. Additionally, some polymers have a "sticky" or "tacky" nature. If the polymeric material either increases the coefficient of friction or adheres to the catheter balloon, the effective release of the stent from the balloon upon deflation can be compromised. Severe coating damage at the luminal side of the stent may occur post-deployment, which can result in a thrombogenic surface. Accordingly, there is a need to eliminate or minimize the amount of coating that is applied to the inner surface of the stent. Reducing or eliminating the polymer from the stent luminal surface also reduces total polymer load, which minimizes the material-vessel interaction and is therefore a desirable goal for optimizing long-term biocompatibility of the device.

A known method for preventing the composition from being applied to the inner surface of the stent is by placing the stent over a mandrel that fittingly mates within the inner diameter of the stent. A tubing can be inserted within the stent such that the outer surface of the tubing is in contact with the inner surface of the stent. With the use of such mandrels, some incidental composition can seep into the gaps or spaces between the surfaces of the mandrel and the stent, especially if the coating composition includes high surface tension (or low wettability) solvents. Moreover, a tubular mandrel that contacts the inner surface of the stent can cause coating defects. A high degree of surface contact between the stent and the supporting apparatus can provide regions in which the liquid composition can flow, wick and/or collect as the composition is applied to the stent. As the solvent evaporates, the excess composition hardens to form excess coating at and around the contact points between the stent and the support apparatus, which may prevent removal of the stent from the supporting apparatus. Further, upon removal of the coated stent from the support apparatus, the excess coating may stick to the apparatus, thereby removing some of the coating from the stent and leaving bare areas. In some situations, the excess coating may stick to the stent, thereby leaving excess coating composition as clumps or pools on the struts or webbing between the struts. Accordingly, there is a tradeoff when the inner surface of the stent is masked in that coating defects such as webbing, pools and/or clumps can be formed on the stent.

In addition to the above-mentioned drawbacks, other disadvantages associated with dip and spray coating methods include lack of uniformity of the produced coating as well as product waste. The intricate geometry of the stent presents significant challenges for applying a coating material on a stent. Dip coating application tends to provide uneven coatings, and droplet agglomeration caused by spray atomization process can produce uneven thickness profiles. Moreover, a very low percentage of the coating solution that is sprayed to coat the stent is actually deposited on the surfaces of the device. Most of the sprayed solution is wasted in both application methods.

To achieve better coating uniformity and less waste, electrostatic coating deposition has been proposed; and examples thereof are disclosed in U.S. Pat. Nos. 5,824,049 (Ragheb, et al.) and 6,096,070 (Ragheb, et al.). Briefly, for electro-deposition or electrostatic spraying, a stent is grounded and gas is used to atomize the coating solution into droplets as the coating solution is discharged out from a nozzle. The droplets are then electrically charged by passing through an electrical field created by a ring electrode which is in electrical communication with a voltage source. The charged particles are attracted to the grounded metallic stent.

An alternative design for coating a stent with an electrically charged solution is disclosed in U.S. Pat. No. 6,669,980 (Hansen). This patent teaches a chamber that contains a coating formulation that is connected to a nozzle apparatus. The coating formulation in the chamber is electrically charged. Droplets of electrically-charged coating formulation are created and dispensed through the nozzle and are deposited on the grounded stent.

Stents coated with electrostatic techniques have many advantages over dipping and spraying methodology, including, but not limited to, improved transfer efficiency (reduction of drug and/or polymer waste), high drug recovery on the stent due to elimination of re-bounce of the coating solution off of the stent, better coating uniformity and a faster coating process. Formation of a coating layer on the inner surface of the stent is not, however, eliminated with the use of electrostatic deposition. With the use of mandrels that ground the stent and provide for a tight fit between the stent and the mandrel, formation of coating defects, such as webbing, pooling, and clumping, remain a problem. If a space is provided between the mandrel and the stent, such that there is only minimal contact to ground the stent, the spraying can still penetrate into the gaps between the stent struts and coat the inner surface of the stent. Unfortunately, due to the "wrap-around" effect of the electric field lines, charged particles are deposited not only on the outer surfaces of the stent but also are attracted to the inner surfaces.

SUMMARY OF THE INVENTION

Accordingly, directed to remedying the problems in the prior art, disclosed herein are methods for coating abluminal surfaces of stents and other implantable medical devices, as well as systems and apparatuses for carrying out these methods. Brief summaries of various inventions of this disclosure are set forth below.

A stent coating method is disclosed herein which includes the following steps: positioning an elastic porous sleeve over a radially-expandable rod assembly; positioning a stent over the sleeve; radially expanding the rod assembly and thereby pressing the sleeve against an inner surface of the stent in a coating position; and with the sleeve in the coating position, applying a coating material on outer surfaces of the stent.

A medical device coating apparatus is disclosed which includes a rod construction having a distal end, a proximal end and a central portion between the ends; the central portion being radially expandable; the proximal end having an opening aligned with a longitudinal passageway of the central portion; a guide assembly having a proximal end opening and a guide passageway; and the guide passageway being aligned with the longitudinal passageway such that an expansion mandrel inserted into the end opening, through the guide passageway and into the central portion causes the central portion to radially expand.

Also disclosed herein is a coating method which includes the following steps: positioning an absorbent sleeve inside a tubular medical device insert member; and with the sleeve against an inside surface of the insert member, depositing a coating on an outside surface of the insert member.

Further, a method of coating an implantable medical device is disclosed which includes the following steps: with an elastic porous sleeve inside an implantable medical device, expanding the sleeve against an inside surface of the medical device; and after the expanding, applying a coating material on outside surfaces of the medical device.

Even further, a coating system for an implantable tubular medical device is disclosed which includes positioning means for positioning an absorbent or porous member against an inside surface of an implantable tubular medical device; and coating means for coating an outside surface of the medical device with the absorbent or porous member positioned against the inside surface by the positioning means.

Additionally disclosed herein is a coating method which includes expanding an absorbent expandable device within a tubular medical device so that the expandable device is against an inside surface of the medical device in a coating position; and with the expandable device in the coating position, depositing a coating on an outside surface of the medical device.

Further disclosed herein is an application method which includes applying a coating material on abluminal surfaces of a stent with a porous device disposed in the stent.

Even further, a coating application apparatus for stents and the like is disclosed which includes a porous elastic sleeve having a thickness between 0.002 and 0.010 inch, and made of a material having a porosity between 5% and 60%. The sleeve can have an outer diameter of 0.050 to 0.070 inch for a typical coronary stent and a length of between 3⁄16 inch (or about 5 mm) and 2.00 inches. For peripheral stents, the sleeve can have a larger diameter in the range of 0.190 to 0.400 inch (or five to ten mm) and a length in the range of twenty-eight to one hundred millimeters.

Other objects and advantages of the present invention will become more apparent to those persons having ordinary skill in the art to which the present invention pertains from the foregoing description taken in conjunction with the accompanying drawings.

DETAILED DESCRIPTION OF PREFERRED EMBODIMENTS OF THE INVENTION

Figure 1:
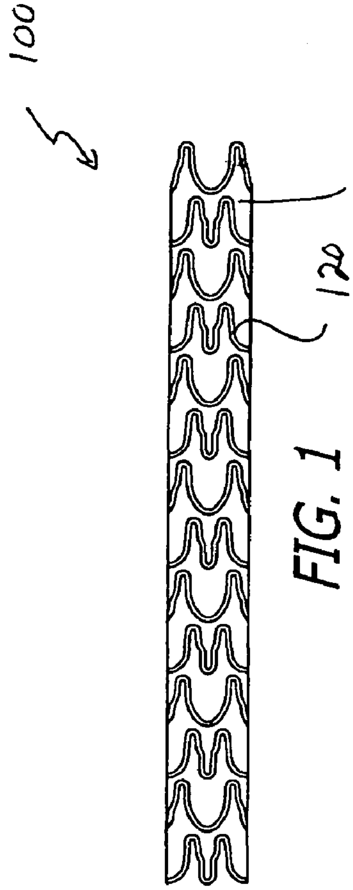
FIG. 1 (PRIOR ART)
FIG. 1 is a plan view of an exemplary prior art stent.

Referring to the drawings wherein like reference numerals designate like parts, systems, apparatuses and methods of the present invention for coating abluminal surfaces of stents and other implantable medical devices are illustrated.

Figure 2:
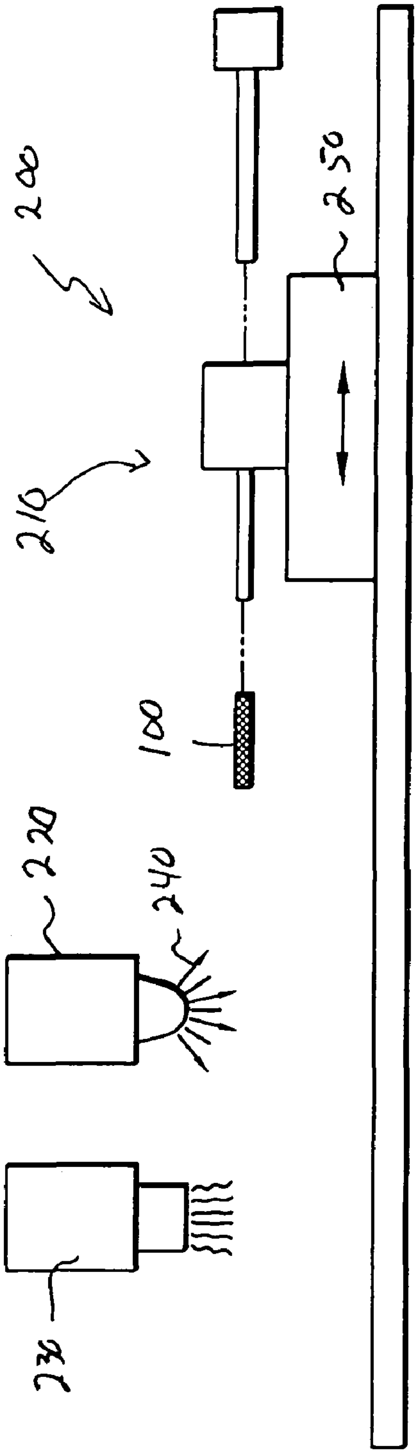
FIG. 2 is a schematic view of a system of the present invention for coating abluminal surfaces of a stent, such as that of FIG. 1, or other implantable medical devices.

A system of the present invention is illustrated schematically generally at 200 in FIG. 2. System 200 includes an apparatus 210 for holding a stent. The stent can be stent 100 or various stents available from Guidant Corporation such as the VISION stent, the PENTA stent, the S stent, peripheral natural stents and plastic stents. The apparatus 210 moves the stent 100 while rotating it underneath a spray coating device 220 and under a heating or drying device 230 and back and forth through a desired number of spraying and drying cycles to apply a coating 240 (FIG. 6) on the stent. A computer controlled motor for moving the apparatus in translation and in number rotation is shown generally at 250. The details of the construction and operation of the system 200 would be apparent to those skilled in the art from this disclosure and from U.S. patent application Ser. No. 10/322,255 filed Dec. 17, 2002 and entitled "Nozzle for Use in Coating a Stent," and U.S. patent application Ser. No. 10/315,457 filed Dec. 9, 2002 and entitled "Apparatus and Method for Coating and Drying Multiple Stents," U.S. Patent Application Publications US 2003/020719 1 (Shekalim, et al.) and US 2004/0013792 1 (Epstein, et al.), as well as the EFD N1537 (EFD Inc., East Providence, R.I.) spray coater.

The duration of the coating time depends on the required coating weight on the stent. For example, to apply six hundred micrograms of coating 240 on an eighteen mm VISION stent 100 using an air-assisted spray method may require ten to twenty spray and drying cycles. In general, the spray time is ten seconds per cycle and the drying time varies from ten to twenty seconds per cycle. The stent 100 can be rotated at a rate of twenty to one hundred or two hundred revolutions per minute, or typically sixty revolutions per minute, during these cycles.

Figure 3:
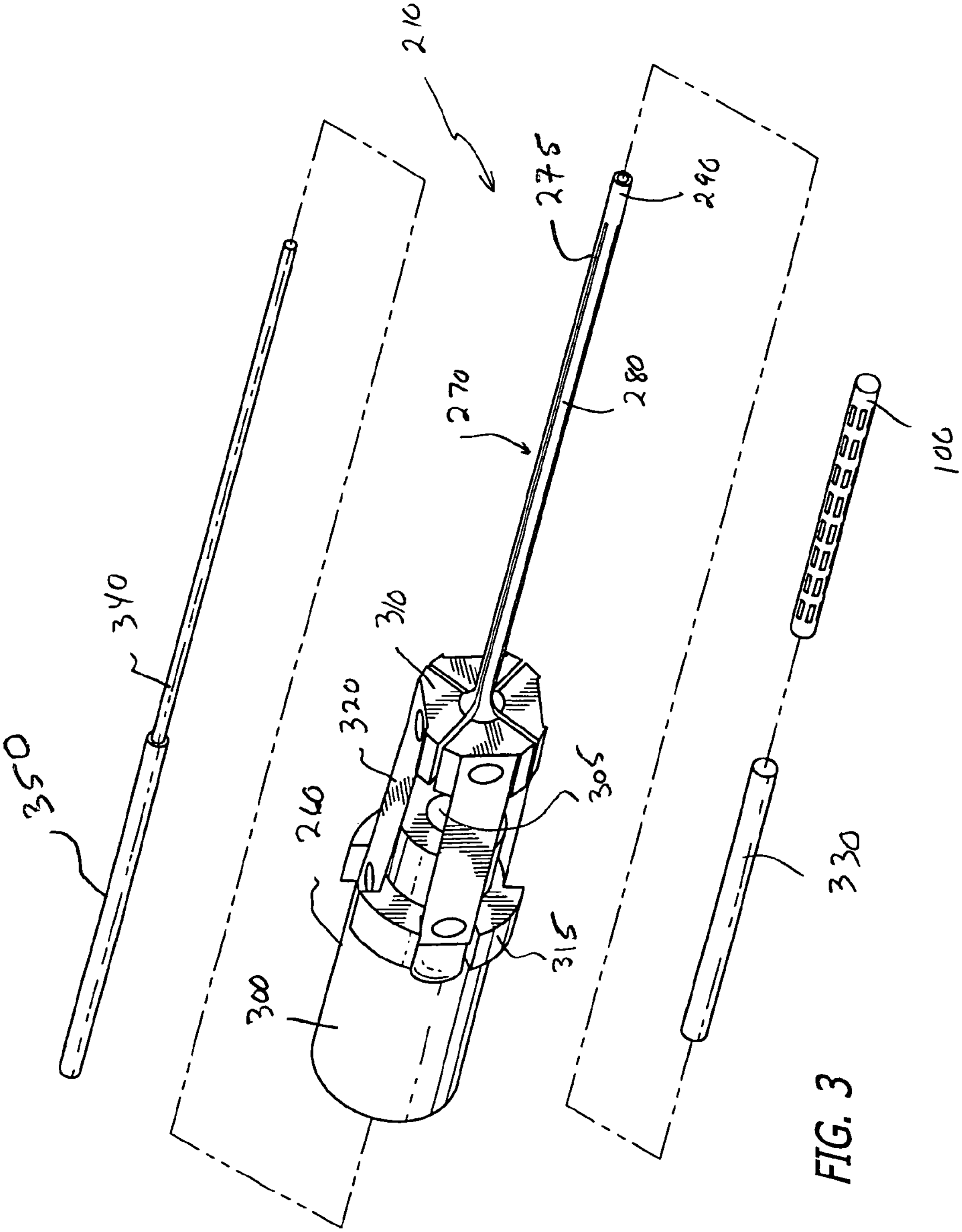
FIG. 3 is an enlarged perspective view of the rod assembly of the system of FIG. 2, showing in exploded relationship the mandrel, the elastic absorbent sleeve and a stent.
Figure 4:
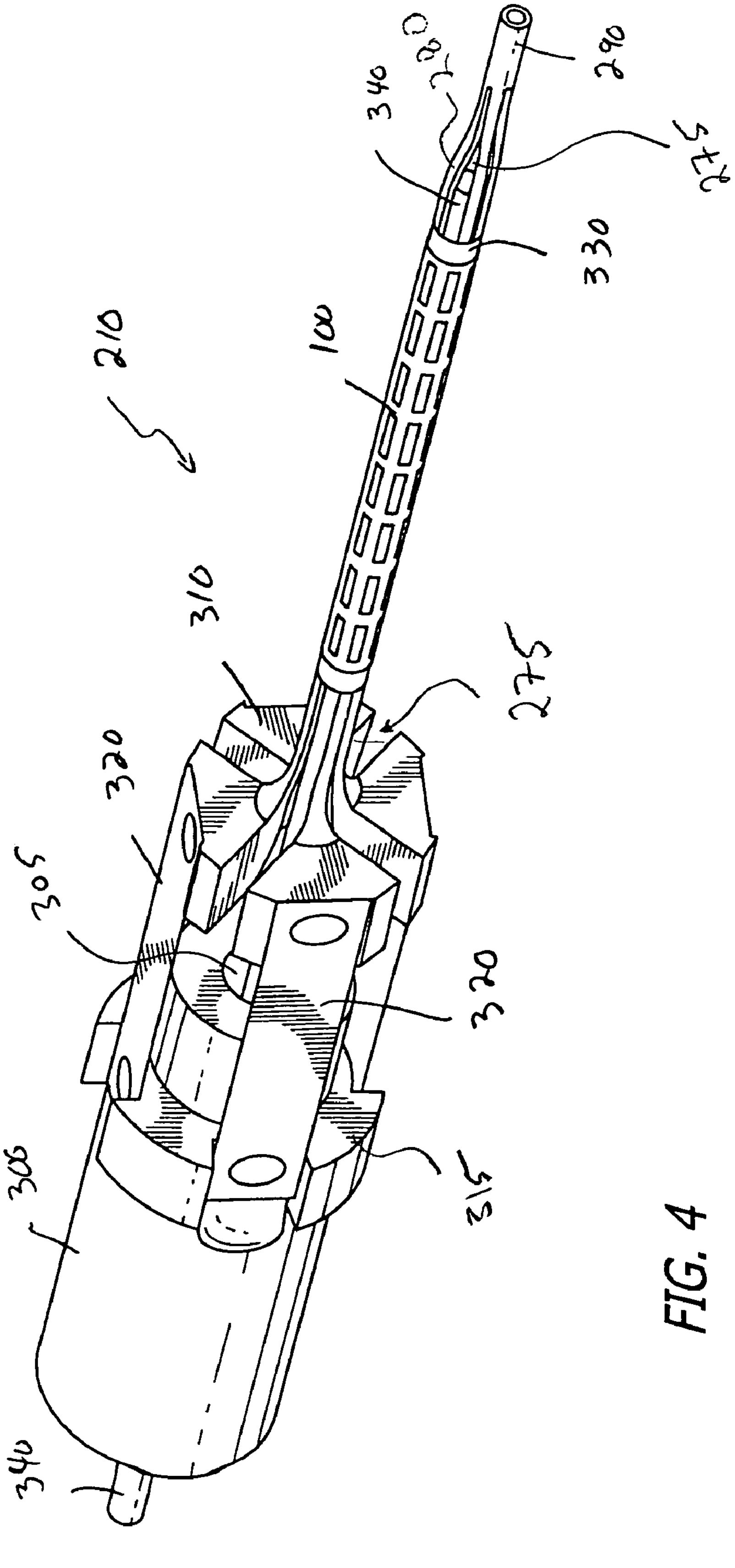
FIG. 4 is an enlarged perspective view of the components of FIG. 3 illustrated in assembled relation.

The apparatus 210 itself is shown in isolation in FIG. 4 and in exploded view in FIG. 3. Referring thereto, it is seen that a chuck 260 is provided having a hollow elongate tube or rod 270 extending out the forward end thereof. In some embodiments, the rod 270 is a stainless steel hypo-tube. The elongated tube 270 includes slots 275 so as to provide for arm members or slotted portions 280 of the elongated tube 270 which can be outwardly expandable with the application of a force. In some embodiments, the elongated tube 270 can terminate at an end ring or sleeve segment 290 with a fixed diameter. The slots 275 do not extend into the end ring or sleeve segment 290. The chuck 260 includes a rear member 300 having an end opening (not shown) leading to a center passageway 305 of the chuck 260. The center passageway 305 is aligned with the hollow bore of the rod 270 so as to allow for a mandrel to be slidably inserted into and withdrawn from the rod 270. The forward portion of the chuck includes segments 310 uniformly spaced apart from one another. Segments 310 are spaced from rear member 300. Segments 310 can be coupled to or can be extensions of their respective arm members 280. Slots 275 also provide gaps between the respective segments 310. The segments 310 are connected by flexible strips 320 (e.g., spring steel) to a ring extension 315 disposed around the rear member 300. Ring extension 315 can be a separate piece or the same piece and carved out from the rear member 300. As is best illustrated in FIGS. 3 and 4, ring extension 315 includes slots for receiving the strips 320 around the periphery of the ring extension 315. The flexible strips 320 allow for radial biasing of arm members 280.

Figure 5:
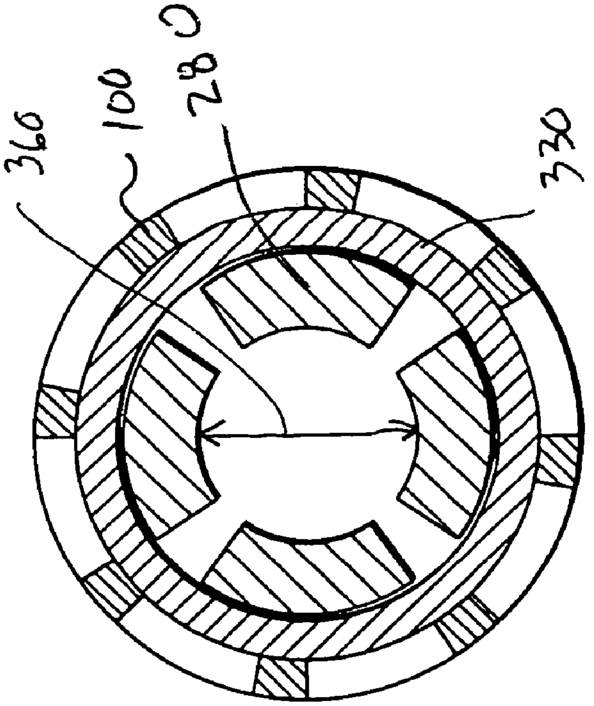
FIG. 5 is an enlarged cross-sectional view of the rod portion of the assembly of FIG. 3 with the sleeve and stent positioned thereon.

An elastic porous and/or absorbent sleeve 330 of the present invention (whose construction and use are disclosed in greater detail later) is fitted over the elongated rod 270 and onto the slotted tube portion 280, and then the stent 100, which is to be coated, is fitted over the sleeve 330. Preferably, the stent 100 is centered over the sleeve 330 and the sleeve 330 has a longer length than that of the stent 100, as can be understood from FIG. 4. A mandrel 340 is held by its enlarged handle portion 350 and inserted into the opening in the rear face of the rear chuck member 300 and into the expandable slotted tube portion 280. The mandrel 340 can be manually or mechanically inserted. The mandrel 340 is sized to have an outside diameter larger than the inside diameter of the elongated tube 270. The inside diameter is designated by reference numeral 360 in FIG. 5, and the mandrel diameter is designated by reference numeral 370 in FIG. 6.

Figure 6:
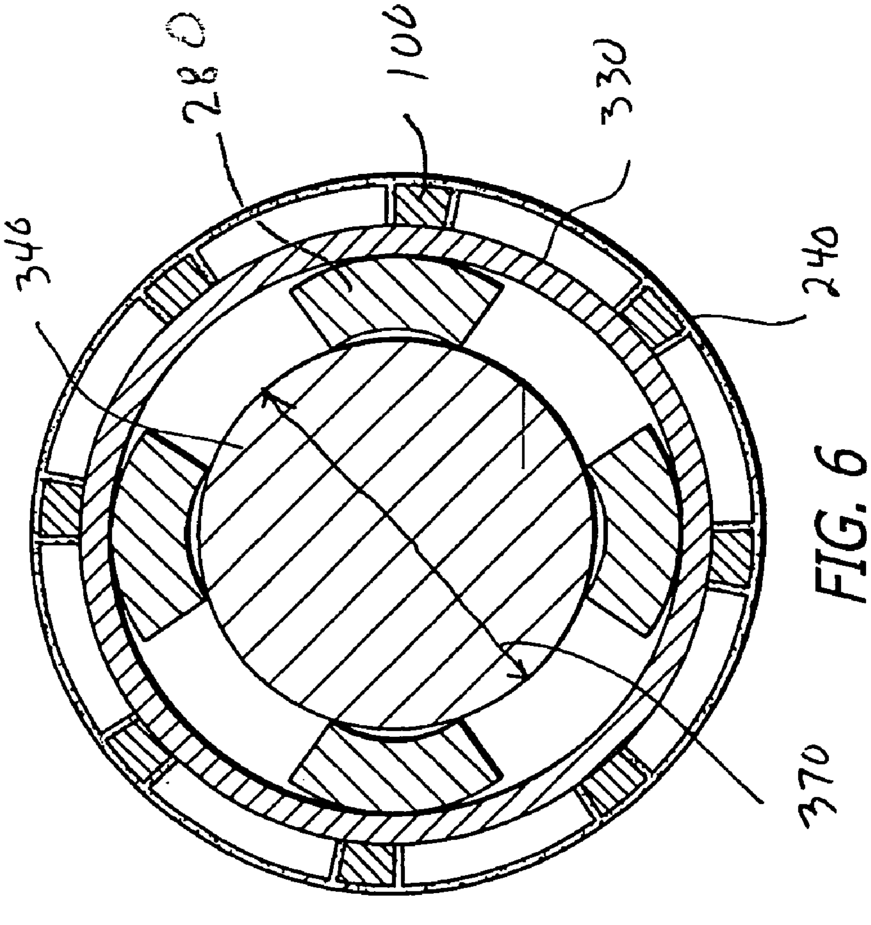
FIG. 6 is a view similar to FIG. 5 with the expansion mandrel inserted therein and the coating applied to the stent.

Since the mandrel diameter 370 is larger than the tube diameter 360, the slotted tube portion 280 will be caused to radially expand when the mandrel 340 is inserted therein. This expansion can be understood by comparing FIG. 6 with FIG. 5. The sleeve 330 is thereby pressed against the inside surface of the stent 100 as shown in FIG. 6. In some embodiments, the force applied to the stent can also cause the stent to expand, as shown in FIG. 6. The sleeve 330 is firmly pressed against the inside surface (the luminal surface) of the stent 100. The coating 240 is then sprayed or otherwise deposited onto the abluminal surfaces of the stent 100.

The sleeve 330 firmly pressed against the inside surface of the stent 100 prevents the (liquid) coating 240 from contacting the luminal surfaces of the stent 100, as can be understood from FIGS. 4 and 6. The coating material 240 will be described in detail later in this disclosure. The sleeve 330 can have a length between 3/16 inch (or about five m) and two inches to accommodate the stent length, a thickness between 0.002 and 0.010 inch and an outer diameter of between 0.050 and 0.070 inch, for example, to be the same as the inner diameter of the stent. In some embodiments, the diameter can be between 0.060 and 0.070 inch. The outer diameter of the sleeve 330 can be selected to be the same as the inner diameter of the stent 100. For peripheral stents, the sleeve can have a larger diameter in the range of 0.190 to 0.400 inch (or five to ten mm) and a length in the range of twenty-eight to one hundred millimeters. In some coating applications such as for very tight stent geometries, the stent 100 can be or must be pre-expanded to a larger size for easy coating. The coated stent can be crimped later on the catheter. In such cases, the sleeve 330 dimensions need to be tailored to fit the needs of that specific application. The length of the sleeve 330 depends on the length of the stent 100 to be coated. A common length of a stent 100 is between approximately five mm to thirty-eight mm. The overall length of the sleeve 330 can be one and a half to two times longer than the length of the stent 100. For easy operation, the sleeve 330 can be trimmed so that its length covers the entire expansion section. In other words, the length of the sleeve 330 can be up to three inches (or seventy-six mm), for example.

The common inside diameter of a coronary stent 100 (made of 316L stainless steel or CoCr material) is in the range of 0.050 inch to 0.070 inch. A thin elastic porous sleeve 330 can be made to close to the stent ID. The expansion mandrel 340 can also be made to the size to allow the radial expansion of the sleeve evenly to appose the luminal side of the stent. Preferably, the change on the diameter of the stent 100 should be kept to a minimum (for example, less than 0.010 inch). The subsequent step, crimping on the stent of the catheter, will bring the stent down to an even smaller size than the original stent size (the "profile" of the product, such as 0.040 inch, and it needs to be kept as small as possible). In most cases, the stent can be expanded further prior to the coating process to facilitate the process (since the coated stent will be crimped on the catheter, which has a smaller profile, or outside diameter). Nitinol stents (or self-expanding stents) are usually larger in size and are used in peripheral vessels of the body which have larger ID. The Nitinol stent is coated at its expanded state; then the coated stent is crimped on the catheter using a restraining sheath. Since Nitinol stents have shape memory, they can be squeezed or enlarged, and they will go back their original size once the applied force is released. In both cases, the dimension change of the stent depends upon the mandrel 340 used. In some cases, a larger size mandrel can be used to increase the distance between the struts of the stent to avoid the coating defect between the struts (excess materials between the struts may cause the webbing).

The sleeve 330 can be made of a material having a porosity between 1% and 60%, between 5% and 60%, between 10% and 50%, or between any range therein depending on the coating formulation used. In some embodiments, the sleeve 330 can be made from an absorbent material capable of taking or sucking up at least some of the material exposed to the sleeve 330. In some embodiments, a combination of porous and absorbent material can be used. Since most coating formulations contain an organic solvent or a mixture of solvents, the material of the sleeve 330 should be solvent resistant and non-stick. Good candidate materials include fluoropolymers (such as polytetrafluoroethylene (PTFE), fluorinated ethylene propylene polymers (FEP) and PFA) and polyolefin materials (such as polyethylene and polypropylene). The sleeve 330 can be made in a thin tube or sheet form. One example is to use expanded polytetrafluoroethylene (e-PTFE) for the sleeve material because of its nonstick nature. For aqueous base coating, the sleeve material can be expanded to include any porous elastic material, such as polyurethane foams, polystyrenes, cottons and rubbers. Sponges can also be used for the sleeve 330.

The components of the coating substance or composition can include a solvent or a solvent system comprising multiple solvents; a polymer or a combination of polymers; and/or a therapeutic substance or a drug or a combination of drugs. Representative examples of polymers that can be used to coat a stent or other medical device include ethylene vinyl alcohol copolymer (commonly known by the generic name EVOH or by the trade name EVAL); poly (vinylidene fluoride-co-hexafluoropropylene) (PVDF-HFP); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); co-poly(ether esters); polyalkylene oxalates; polyphosphazenes; biomolecules, such as fibrin, fibrinogen, starch, collagen and hyaluronic acid; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof. In the case of electro spraying, solvents should have a high enough conductivity to enable ionization of the composition if the polymer or therapeutic substance is not conductive. For example, acetone and ethanol have sufficient conductivities of $8\times10^{-6}$ and $\sim10^{-5}$ siemen/m, respectively.

Examples of therapeutic substances that can be used include antiproliferative substances such as actinomycin D, or derivatives and analogs thereof (manufactured by Sigma-Aldrich of Milwaukee, Wis.). The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by everolimus and available from Novartis), 40-O-(3-hydroxy)propyl-rapamycin, 40-O-[2-(2-hydroxy)ethoxy] ethyl-rapamycin, and 40-O-tetrazole-rapamycin. Various medical device coatings are disclosed in U.S. Pat. No. 6,746,723 (Llanos, et al.), and U.S. Patent Application Publication US 2004/0142015 (Hossainy, et al.).

In conclusion, potential benefits of coating abluminal surfaces of stent 100 include: reducing the usage of drug and polymer; minimizing the systemic effects of drugs from stent luminal surfaces; preventing the luminal side of coating from flaking off during the procedure, which may cause severe downstream embolization; minimizing the interaction between the luminal coating and balloon material (coating delamination in the luminal side); and protecting the existing luminal coating (in some cases, different drugs may need to be applied at stent luminal surface).

Techniques being evaluated to achieve abluminal coating include: atomized spraying, direct dispensing (auto-caulking) or micro-dispensing, roll coating, electrospray; and hand dispensing. Challenges for these techniques include: stent geometry (strut is too thin); stent and its mandrel (damage on coating); coating throughput (for auto-caulking); and formulation dependent (viscosity, volatility, conductivity of the solvent, etc.).

To meet these challenges and as discussed above, an expander or a balloon design (such as e-PTFE balloon) can be utilized to expand a thin, porous or absorbent elastic sleeve 330 (polyurethane, polyolefin, or e-PTFE tube) to fully support the stent 100 and to prevent the coating material from contacting the luminal side of the stent. An elastic absorbent material is a preferred material to fully support stent luminal surface and to act as a reservoir for the excess material in the stent opening areas 160 (the non-strut sections), by absorbing or by permeating through the pores. Upon completing the coating, the expander or balloon is deflated to its original smaller dimension to release the coated stent.

More specifically, a thin porous elastic sleeve 330 (PP or PE material from Micropore Plastics, Inc., or Zeus for e-PTFE material) and a stent 100 are positioned over the expander 280 and an expansion mandrel 340 (with the appropriate size) is inserted into the expander to expand the sleeve 330 to fully support the luminal surface of the stent. This assembly can then be placed onto a coater for receiving coating on the abluminal side of the stent. One or more coatings can be applied by using conventional air-assisted spray methods, electrosprays, or roll coatings (or it may help in auto caulker applications). (See FIG. 2.)

A second technique includes a balloon with a porous surface structure (such as an e-PTFE or expanded polyethylene balloon) or a balloon is used to expand a porous or absorbent elastic sleeve to support and block the stent luminal surface from the coating material. A balloon can be inflated to the internal diameter of the stent to fully support the luminal surface of the stent. The coating can then be applied to the stent by using convention air-assisted spray methods, electrospray methods, a roll coating device or other contacting transfer methods, or micro-dispensing equipment such as drop-on-demand types of drop ejectors.

These techniques can be applied to current and future drug coated stents. They may improve drug and polymer usage efficiency substantially, and they enable stent abluminal surfaces to be coated. They also provide flexibility to tailor coating designs.

Further, these techniques can be applied to coat any metallic (self-expanding or balloon expandable) or plastic stent (which is made of durable or bio-absorbable polymer), including neurological, coronary, peripheral, and urological stents. They can also be used to coat other tubular (or spiral) medical devices, such as grafts and stent-grafts. Metallic materials from which a stent can be made and coated include, but are not limited to 316L stainless steel, 300 series stainless steel, cobalt chromium alloys, nitinol, magnesium, tantalum, tantalum alloys, platinum iridium alloy, Elgiloy, and MP35N. The polymeric materials include, but are not limited to, common plastic materials, fluorinated polymers, polyurethanes, polyolefins, polysulfones, cellulosics, polyesters (biodegradable and durable), PMMA, polycarbonate, and tyrosine carbonate. Other non-metallic non-polymeric devices, such as fibrin stents, and ceramic devices, also fall within the scope of the invention.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A stent coating method, comprising:

positioning an elastic porous sleeve over a radially-expandable rod assembly;

positioning a stent over the sleeve;

radially expanding the rod assembly and thereby pressing the sleeve against an inner surface of the stent and into a coating position; and with the sleeve in the coating position, applying a coating material on outer surfaces of the stent, wherein the rod assembly includes a slotted tube and a chuck attached to the slotted tube, and the expanding includes inserting a mandrel through the chuck and into the slotted tube.

2. The method of claim 1 wherein the expanding radially expands the stent.

3. The method of claim 1 wherein the positioning the sleeve is before the positioning the stent.

4. The method of claim 1 wherein the pressing includes fully supporting the stent and thereby preventing the coating material from contacting the luminal side of the stent.

5. A coating method, comprising:

positioning an absorbent sleeve inside a tubular medical device insert member; and with the sleeve against an inside surface of the insert member, depositing a coating on an outside surface of the insert member, wherein the positioning includes radially expanding the sleeve against the inside surface of the insert member, and the expanding includes with the sleeve disposed on a slotted tube and the insert member disposed on the sleeve, inserting an expansion tool in the slotted tube.

6. The method of claim 5 wherein the depositing includes successive spray coating and drying steps.

7. The method of claim 5 wherein the coating includes at least one of a polymer and a therapeutic substance.

8. The method of claim 5, wherein the slotted tube includes a plurality of portions that move apart from each other when the expansion tool is inserted in the slotted tube.

9. The method of claim 5, wherein the insert member is a stent.

10. A coating method, comprising:

with an elastic porous sleeve inside an implantable medical device, expanding the sleeve against an inside surface of the medical device; and after the expanding, applying a coating material on outside surfaces of the medical device, wherein the expanding includes positioning the sleeve onto an elongate expander device and the medical device over the sleeve, and after the positioning, radially expanding the expander device, the expander device including a slotted tube, a chuck attached to the slotted tube, and a mandrel configured to slide through the chuck and into the slotted tube.

11. The method of claim 10 further comprising after the applying, contracting the sleeve and removing the sleeve from the medical device.

12. The method of claim 11, wherein the contracting includes removing an expansion tool from the expander device.

13. The method of claim 10 wherein the radially expanding includes inserting an expansion tool into the expander device.

14. The method of claim 10 wherein the medical device is a stent.

15. The method of claim 14 wherein the stent is a self-expanding stent.

16. The method of claim 14 wherein the stent is a balloon expandable stent.

17. The method of claim 10 wherein the coating material includes at least one of a polymer and a therapeutic substance.

18. The method of claim 10 wherein the expanding causes the medical device to radially expand.

19. A coating method, comprising:

expanding an absorbent expandable device within a tubular medical device so that the expandable device is against an inside surface of the medical device and thereby in a coating position; and with the expandable device in the coating position, depositing a coating on an outside surface of the medical device, wherein the expandable device is an elastic porous sleeve and the expanding includes inserting an expansion tool inside of the sleeve, and wherein the sleeve is disposed over a slotted tube, and the inserting step includes inserting the expansion tool in between portions of the slotted tube to move the portions of the slotted tube apart from each other.

20. The method of claim 19 wherein the medical device is a stent.

21. The method of claim 19 wherein the depositing includes the coating having at least one of a polymer and a therapeutic substance.

22. An application method, comprising:

applying a coating material on abluminal surfaces of a stent with an expanded porous device disposed in the stent and pressed against luminal surfaces of the stent, wherein before the applying step, the porous device is expanded by inserting a structure into the porous device, wherein the porous device includes a sleeve, and further comprising the step of positioning the sleeve over an expandable device before the applying step, and wherein the expandable device includes a plurality of portions extending through the sleeve, the portions configured to move relative to each other.

23. The method of claim 22 wherein the expanding of the porous device causes radial expansion of the stent.

24. The method of claim 22 wherein the porous device is an elastic porous sleeve.

25. The method of claim 22 wherein the applying includes successive coating material spraying and drying steps.

26. The method of claim 22, wherein before the applying step, the porous device is positioned over an expandable device having a central passageway.

27. The method of claim 26, wherein the inserting step includes inserting the structure in the passageway to expand the expandable device and the porous device before the applying step.

28. The method of claim 26, further comprising withdrawing the structure from the passageway to contract the expandable device and the porous device after the applying step.

29. The method of claim 22, wherein the inserting step includes inserting the structure in between the portions to move the portions apart from each other before the applying step.

30. The method of claim 22, further comprising withdrawing the structure from between the portions to allow the portions to move toward each other after the applying step.

* * * * *